United States Patent
Shaw et al.

(10) Patent No.: US 8,362,286 B2
(45) Date of Patent: Jan. 29, 2013

(54) METHOD FOR MAKING 3α-HYDROXY, 3β-SUBSTITUTED-5α-PREGNAN-20-ONES

(75) Inventors: Kenneth Shaw, Weston, CT (US); Alan Hutchison, Brick, NJ (US)

(73) Assignee: Marinus Pharmaceuticals, Inc., Branford, CT (US)

( * ) Notice: Subject to any disclaimer, the term of this patent is extended or adjusted under 35 U.S.C. 154(b) by 105 days.

(21) Appl. No.: 12/854,226

(22) Filed: Aug. 11, 2010

(65) Prior Publication Data

US 2011/0040112 A1  Feb. 17, 2011

Related U.S. Application Data

(60) Provisional application No. 61/233,553, filed on Aug. 13, 2009.

(51) Int. Cl.
*C07J 7/00* (2006.01)
(52) U.S. Cl. ........................................ 552/603
(58) Field of Classification Search .................. 552/603
See application file for complete search history.

(56) References Cited

U.S. PATENT DOCUMENTS

| | | | |
|---|---|---|---|
| 3,953,429 A | 4/1976 | Cook et al. | |
| 5,319,115 A | 6/1994 | Tahir et al. | |
| 6,117,994 A | 9/2000 | Geurts et al. | |
| 7,858,609 B2 * | 12/2010 | Shaw et al. | 514/183 |
| 8,022,054 B2 * | 9/2011 | Shaw et al. | 514/183 |
| 2007/0141161 A1 | 6/2007 | Shaw et al. | |

FOREIGN PATENT DOCUMENTS

| WO | 2006010085 A1 | 1/2006 |
|---|---|---|
| WO | 2007062266 A3 | 5/2007 |

OTHER PUBLICATIONS

International Search Report for International Application No. PCT/US2010/045176 dated Apr. 14, 2011.
Written Opinion for International Application No. PCT/US2010/045176 dated Apr. 14, 2011.
He, et al., "Synthesis of ganaxalone," Chinese Journal of New Drugs, 14(8): 1025-1026 (2005) (translation of abstract only).
Hogenkamp, et al., "Synthesis and in vitro Activity of 3(beta)-Substituted-3(omega)-hydroxypregnan-20-ones: Allosteric Modulators of the GABAA Receptor," J. Med. Chem. 40: 61-72 (1997).
Johnson, et al., "The Mechanism of Nucleophilic Alkylidene Transfer by Sulfonium and Oxosulfonium Ylides," J. Am. Chem. Soc. 95(22): 7424-7431(1973).
Kauffmann, et al., "Nichtstabilisierte Eisenalkyle: Bildung, Nachweis und Chemoselektivitat," Chem. Ber. 125: 163-169 (1992).
Nohria, et al., "Ganaxolone," Neurotherapeutics: 4(1): 102-105 (2007).
Reetz, et al., "Unprecedented Stereoselectivity in the Addition of Organoiron(II) Reagents to Cyclohexanone Derivatives," J. Chem. Soc. Chem. Commun., 328-330 (1993).
Reetz, et al., "Ligand Effects in Selective Carbonyl Addition Reactions of Organomanganese and Cerium Reagents," Tetrahedron Letters 33(46): 6963-6966 (1992).
International Preliminary Report on Patentability for International Application No. PCT/US2010/045176, International Filing Date Aug. 11, 2010, Date of Issuance of Report Feb. 14, 2012, 7 pages.

\* cited by examiner

*Primary Examiner* — Sabiha Qazi
(74) *Attorney, Agent, or Firm* — Cantor Colburn LLP

(57) ABSTRACT

Applicants have discovered a method for the stereoselective and regioselective synthesis of 3α-hydroxy, 3β-methyl-5α-pregnan-20-one (ganaxolone) comprising reacting 5α-pregnane-3,20-dione; with an organometallic methylating agent in an inert solvent to provide a compound of the formula

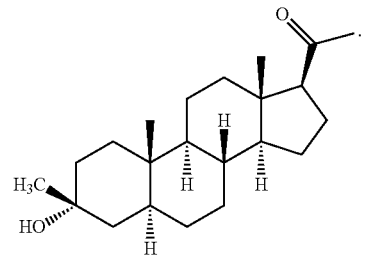

23 Claims, 1 Drawing Sheet

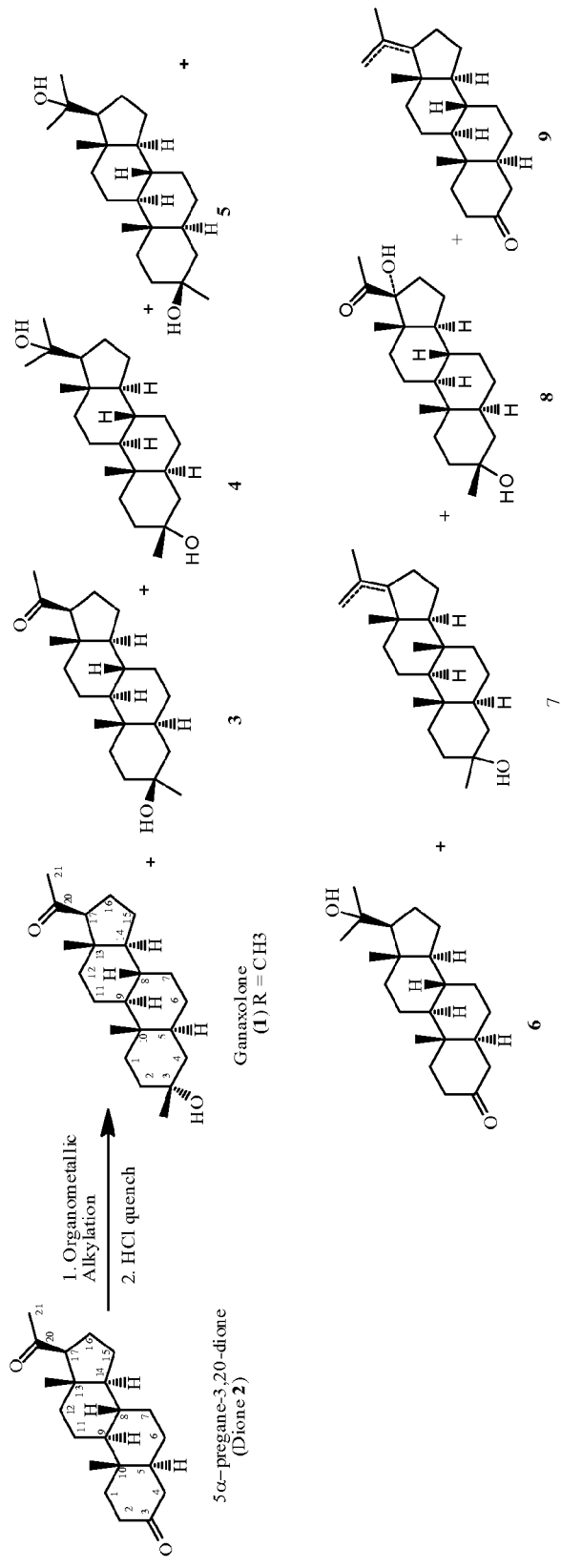

METHOD FOR MAKING 3α-HYDROXY, 3β-SUBSTITUTED-5α-PREGNAN-20-ONES

CROSS REFERENCE TO RELATED APPLICATION

This application claims priority from U.S. Provisional Patent Application No. 61/233,553, filed Aug. 13, 2009, which is hereby incorporated by reference in its entirety.

BACKGROUND OF THE INVENTION

A number of 3α-hydroxy, 3β-substituted-5α-pregnan-20-ones steroid derivatives have proven effective in modulating the GABA receptor chloride ionophore complex (GR complex) in vitro and exhibit useful therapeutic effects in animal models of human CNS disorders. Foremost among them is 3α-hydroxy, 3β-methyl-5α-pregnan-20-one (Ganaxolone, GNX, 1) which has been shown to stimulate the GR complex and demonstrates a variety of beneficial physiological effects in vivo. Ganaxolone 1 is being tested in advanced clinical trials for epilepsy and may have utility in a number of other CNS disorders. The high doses of ganaxolone required for efficacious treatment in humans (>1 g/day) necessitate the need for an efficient and low cost manufacturing process (Nohria and Giller, J. Am. Soc. Exp. Neurotherapeutics, (2007) 4: 102-105).

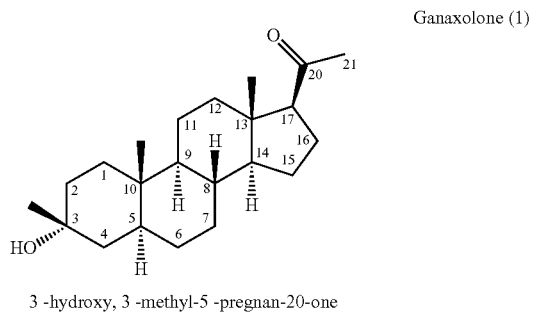

Ganaxolone (1)

3-hydroxy, 3-methyl-5-pregnan-20-one

The most direct approach to the synthesis of ganaxolone is via regioselective and stereoselective attack at the C-3 carbonyl of 5α-pregnane 3,20-dione (Dione 2) by an organometallic methylating agents such as methyl Grignard or methyllithium. Direct methylation of 5α-pregnane 3,20-dione with methyllithium or methyl Grignard to prepare ganaxolone has not been possible as irreversible attack of both the C3 and C20 carbonyl groups by carbon anions yields complex mixtures of products.

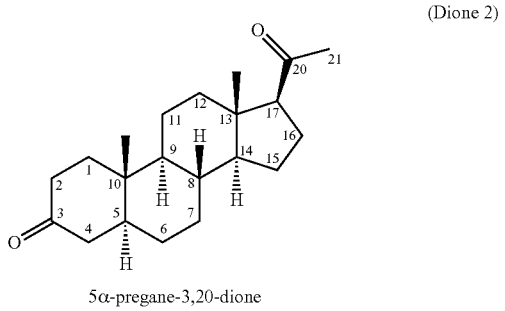

(Dione 2)

5α-pregane-3,20-dione

As the undesired products from methylation of dione 2 have similar physical properties to of ganaxolone, one must obtain ganaxolone from an organometallic methylation reaction of Dione 2 with less than 10% of any single impurity to avoid multiple purification steps which also lower the effective yield and increase the manufacturing costs to obtain pharmaceutically pure ganaxolone (no single impurity >0.1%).

The standard approach to the synthesis of Ganaxolone 1 involves protection of the C-20 carbonyl of 3α-hydroxy-5α-pregnane 20-one prior to oxidation to react with an organometallic methylating agent at position 3 to introduce the 3β-methyl group followed by hydrolysis of the ketal at C-20 (Hogenkamp et al., J. Med. Chem., (1997) 40: 61-72). The disadvantage of this approach is that it adds at least two additional steps to the overall synthesis, first protection of the C20 carbonyl, removal of the protecting group after introduction of the 3β-methyl group.

More importantly, the stereoselectivity is quite poor resulting in nearly equal amount of the 3α and 3β isomers. This increases the cost and complexity of the synthesis and lowers the overall yield for the process.

Another method for the synthesis of ganaxolone (1) is provided by U.S. Pat. No. 5,319,115 and the literature (He et. al., Zhongguo Xinyao Zazhi (2005), 14(8), 1025-1026) wherein dione 2 is reacted with Corey's Reagent (trimethylsulfoxonium iodide) and potassium t-butoxide in tetrahydrofuran via a reversible thermodynamically controlled reaction (Johnson et al., J. Am. Chem. Soc., (1973), 95 (22), 7424-7431) to generate the more stable epoxide isomer (1-((2'R, 5S,8R,9S,10S,13S,14S,17S)-10,13-dimethylhexadecahydrospiro [cyclopenta[a]phenanthrene-3,2'-oxirane]-17-yl) ethanone) at C3. The epoxide is reduced under a variety of conditions including nucleophilic opening of the epoxide with potassium iodide and reducing the resulting iodide via hydrogenation to afford ganaxolone 1. This synthesis requires isolation and purification of the intermediate epoxide as well as many manipulations and an expensive hydrogenation step all of which contribute to a more expensive and lengthy process. The reaction of Corey's reagent with Dione 2 followed by reduction of the epoxide yields a by-product 17-hydroxyganaxolone 8 which is difficult to remove. Obtaining purified ganaxolone via the Corey reagent route has often produced levels of 17-hydroxyganaxolone >0.1% by HPLC.

There remains a need for an efficient and cost effect ganaxolone synthesis, which provides high purity ganaxolone.

SUMMARY OF THE INVENTION

The invention provides a simple and cost effective method for the manufacture of ganaxolone from 5α-pregnane-3,20-dione.

The inventors have surprisingly discovered that organometallic addition to the 3,20-dione (2) can be performed with both unexpectedly good regioselectivity and stereoselectivity. The inventors discovered that it is possible to achieve regioselective reaction at the C3 carbonyl of Dione 2 with little or no reaction taking place at the C20 carbonyl with appropriate selection of reagents and reaction conditions. The inventors further confirmed that appropriate choice of reagents and conditions can give high stereoselectivity by equatorial attack of the methylating agent to yield the desired beta methyl isomer ganaxolone. Thus in a first aspect, the invention provides a method for the manufacture of ganaxolone comprising reacting 5α-pregnane-3,20-dione (Dione 2);

with an organometallic methylating agent in an inert solvent to provide a compound of the formula (Ganaxolone)

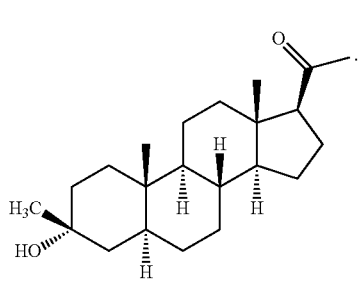

wherein the purity of the ganaxolone is greater than 80 percent pure by HPLC.

The invention also has the advantage of providing ganaxolone in high yield and substantially free of reaction impurities. By the appropriate use of organometallic methylating agent this transformation can be achieved in unexpectedly high chemical yield with high regioselective and stereoselective control. Using this invention no protection of the C20 carbonyl is required and the overall transformation is effected in one chemical step without the need to isolate any intermediates.

The invention further provides a method for manufacture of ganaxolone comprising reacting 5α-pregnane-3,20-dione with an organometallic methylating agent in an inert solvent to provide ganaxolone, which is at least 99.5% pure by HPLC. In certain embodiments, after a single purification step, the ganaxolone obtained contains less than 0.1 percent area by HPLC of any one of the reaction impurities of the formula

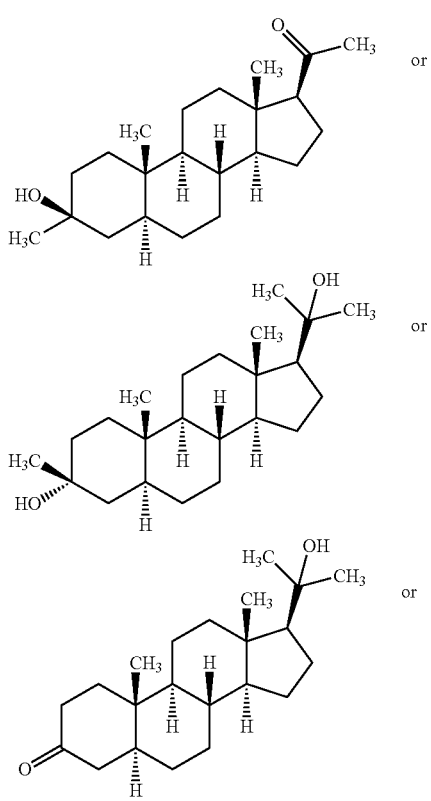

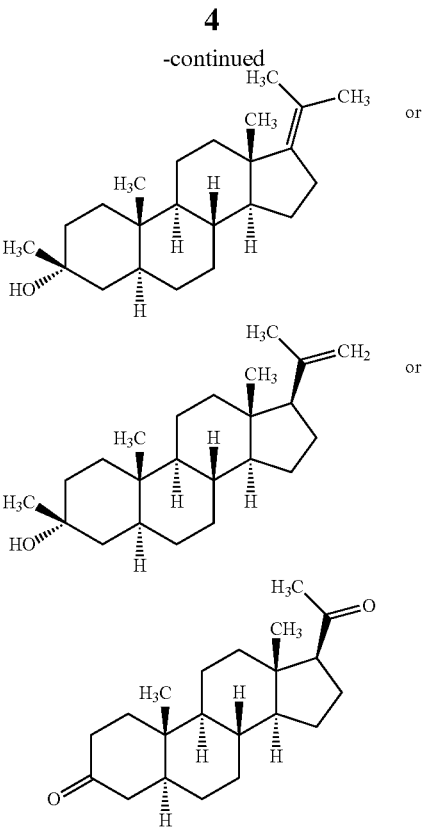

BRIEF DESCRIPTION OF THE DRAWINGS

FIG. 1. Potential Products from Organometallic Addition of Dione 2. Previous methods for preparing ganaxolone via direct methylation of the C3 ketone of dione 2 gave ganaxolone and a variety of reaction impurities as depicted here.

DETAILED DESCRIPTION OF THE INVENTION

Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

"Alkoxy" indicates an alkyl group as defined above with the indicated number of carbon atoms attached through an oxygen bridge (—O—). "Lower alkoxy" typically has from 1 to about 6 carbon atoms and in some preferred embodiments, from 1 to about 3 carbon atoms. An "Ate Complex" is a salt formed by the reaction of a Lewis acid and a base wherein the centralatom in the salt complex increases its valence. Examples of ate complexes include $(CH_3)_3FeLi$ and $(CH_3)_3FeMgCl$.

As used herein "halide" is chloride, bromide, or iodide.

HPLC as used herein is high performance liquid chromatography utilizing refractive index detection with the method described in the Experimental Section.

"Percent pure" ("% purity") refers to the area percentage obtained from dividing the area of the ganaxolone HPLC peak by the sums of areas for the ganaxolone HPLC peak and the HPLC peaks of each reaction impurity and multiplying dividend by 100.

"Percent Yield" or "isolated yield" ("% yield") is the weight of the isolated product(s) divided by the molecular weight of ganaxolone divided by the moles of starting material used in the reaction.

"Reaction Impurities" are process related impurities (by products) including all residual starting materials, residual intermediates, and other reaction products other than ganaxolone detected by HPLC. The FDA uses the term "process related impurities" to describe impurities derived from the manufacturing process.

"Regioselective" is any direct organometallic methylation reaction with 5α-pregnane-3,20-dione that results in less than 10% of C20 adduct 6 identified in FIG. 1.

"Stereoselective" is any direct organometallic methylation reaction on 5α-pregnane-3, 20-dione that results in less than 10% of the undesired epimeric byproduct 3 in FIG. 1.

The transitional phrases "comprising," "consisting essentially of," and "consisting of," carry the meanings accorded these terms by current patent law. All embodiments claimed with one of the transitional phases may also be claimed using the other transitional phrases. For example, an embodiment claimed with "conprising" as the transitional phrase also includes embodiments that may be claimed with "consisting essentially of" or "consisting of" transitional language and vice versa.

Chemical Description

Given the issues suffered by existing ganaxolone synthesis methods, the most cost effective ganaxolone manufacturing method is via direct methylation at the C3 ketone of dione 2. Stereoselective and regioselective attack at C-3 with Corey's Reagent via a reversible thermodynamic process would not be expected to be applicable to the direct irreversible addition of an organometallic reagent to dione 2. A mixture of products is expected from this reaction. This expectation is born out in Example 1 of the Experimental Section wherein dione 2 is reacted with methyllithium in tetrahydrofuran to afford a complex mixture of products (see FIG. 1) which contains only about 11% of the desired product ganaxolone. Process related impurity 7 depicts the possible olefin dehydration products when process related impurities 4 and 5 are subjected to an acidic environment which can induce dehydration of the C21 hydroxy group. Process related impurity 9 depicts the possible olefin positions for dehydration of the C21-hydroxy group from structure 6 upon addition of acid.

The inventors have discovered a single step regioselective and stereoselective ganaxolone synthetic method for the preparation of ganaxolone. The starting materials for this process is 5α-pregnane-3,20-dione whose efficient and cost effective synthesis is known. Reaction of preferred organometallic methylating reagents in an inert solvent with 5α-pregnane-3,20-dione affords the corresponding ganaxolone in one chemical step without any isolable intermediates. The preferred organometallic methylating agent may be a purified and well-characterized material or a mixture of organometallic species generated in situ. The reaction may be run in any inert solvent (or combinations of inert solvents) but most favorably in ethereal solvents such as tetrahydrofuran, glyme, t-butyl methyl ether, 1,4-dioxane, dimethoxyethane or diethyl ether. It is also advantageous to add inorganic salts such as lithium halides to the reaction mixture to further improve the reaction yield and reduce viscosity of the reaction allowing less inert solvent and higher batch size in a reaction vessel. In general the regioselectivity and stereoselectivity of the reaction is a function of solvent, temperature and composition of the organometallic methylating reagent.

In one embodiment the invention includes a method for the manufacture of ganaxolone comprising reacting 5α-pregnane-3,20-dione with an organometallic methylating agent in an inert solvent. In certain embodiments the % yield of ganaxolone is at least 45%, at least 55%, at least 70%, at least 80%, at least 85%, at least 90% yield. In certain embodiments the purity of the 3α-hydroxy, 3β-methyl-5α-pregnan-20-one product is at least 70%, at least 80%, at least 90%, or at least 95% area by HPLC. In certain embodiments the amount of individual reaction impurities 3 to 8 in FIG. 1 as a percent of the total reaction products by HPLC is Not More Than (NMT) 20%, or NMT 10% or NMT 5%, NMT 2%, NMT 1%. It is preferred that the yield of impurities is NMT than 2% each, more preferably NMT 1% each, and still more preferably NMT 0.1% area HPLC. It is also preferred that the yield of impurities 5 and 6 is NMT 1% together.

In one embodiment the organometallic methylating agent is generated by adding between 2 and 5 equivalents of methyl magnesium halide or methyllithium to anhydrous ferric chloride ($FeCl_3$) (Reetz, M., et al., *Tetrahedron Lett.*, (1192) 33(46): 6963-6966 and Reetz., M.T. et al., *J. Chem. Soc., Chem. Comm.*, (1993) 328-330.) or anhydrous $FeCl_2$ (Kauffmann, T., et al., Chem. Ber. (1992) 125; 163-169) in an inert solvent system. This generates several distinct methylating reagents depending on stoichiometry, notably MeFeCl, $Me_2Fe$, $Me_3Fe^-$ Y+ and $Me_4Fe^{(2-)}2Y+$ where Y+ is Li+ and/or [MgX]+(X=Cl, Br or I) depending on whether methylmagnesium halide or methyllithium (or combinations) is used to generate the reagent. The properties of these reagents may be advantageously modified by the addition of inorganic salts such as lithium chloride to the reaction before or after addition of the organometallic agent to the ferric chloride solution.

In another embodiment the iron-methylating complex is generated by adding 3-4 equivalents of a methylmagnesium halide to a solution of anhydrous ferric chloride in tetrahydrofuran containing 0 to 3 equivalents of lithium chloride (based on $FeCl_3$). The first equivalent of methylmagnesium halide reduces $FeCl_3$ to $FeCl_2$. When 4 equivalents of methylmagnesium halide is used (based on $FeCl_3$) the methylating agent is presumably the complex ($Me_3Fe$—MgX+) though it is possible a more complicated mixture of reagents and counterions is the methylating agent. The optimal reaction temperature is between −40° C. and 35° C. for generating the organometallic methylating agent(s).

In another preferred embodiment of the invention the organometallic methylating agent is generated by adding 0.5 to 2 equivalents of ferric chloride (based on Dione 2), 3-4 equivalents methylmagnesium chloride (based on $FeCl_3$) to a solution of 0-2 equivalents LiCl (based on $FeCl_3$) in tetrahydrofuran and maintaining temperatures below about −15° C.

In another preferred embodiment of the invention the organometallic methylating agent is generated by adding 3 equivalents of methyl magnesium halide or methyllithium to a solution/suspension of anhydrous ferric chloride in tetrahydrofuran at temperatures below about −15° C. In certain embodiments the reaction temperature is maintained at about −35° C. to about −15° C. until the reaction is complete. The methylating agent is presumably the complex ($Me_2Fe$) but may be a more complex mixture of iron species. The optimal reaction temperature with Dione 2 is between about −25° C. and about 40° C.

In another embodiment the organometallic methylating agent is generated by adding one to four equivalents of a methylmagnesium halide or methyllithium to the titanium reagent TiXYZT where X, Y, Z and T are the same or different and may be halogen or alkoxy with the proviso that the maximum number of equivalents of organometallic reagent added is no more than the number of halogens in the starting titanium reagent. The subsequent reaction with dione 2 is carried out in an inert solvent and reaction temperatures between −40° C. and 70° C.

In certain embodiments the method for synthesizing ganaxolone additionally comprises adding about 0.1 to about 4 equivalents of lithium chloride (based on $FeCl_3$) to the inert solvent prior to adding 3-4 equivalents of methyl magnesium chloride (based on $FeCl_3$) to the inert solvent.

In certain embodiments the method for synthesizing ganaxolone additionally comprises adding about 0.1 to about 4 equivalents of lithium chloride (based on $FeCl_3$) to the inert solvent prior to adding 3-4 equivalents of methyl magnesium chloride (based on $FeCl_3$) to the inert solvent.

In certain embodiments the method for synthesizing ganaxolone additionally comprises adding about 1 equivalent of methylmagnesium halide or methyllithium (based on Titanium) to a solution of tri($C_1$-$C_3$alkoxy)titanium chloride in and organic solvent and thereby generating the organometallic methylating agent.

In certain embodiments the organometallic methylating agent is dimethyl iron ($Me_2Fe$), methyl triethoxytitanium, methyl chloro diethoxytitanium (($CH_3$)Cl($CH_3CH_2O$)$_2$Ti), methyl trichlorotitanium ($CH_3Cl_3Ti$), tetramethyltitanium (($CH_3$)$_4$Ti), dimethyl dichloro titanium (($CH_3$)$_2$Ti), trimethyl chlorotitanium (($CH_3$)$_3$ClTi), or methyl iron chloride ($CH_3FeCl$).

In other embodiments the organometallic methylating agent is an "ate complex" containing a ($CH_3$)$_3Fe^-$ anion and either lithium or MgX, as the cation, where X is a halide.

In certain embodiments the method for synthesizing ganaxolone additionally comprises adding about 1 equivalent of methylmagnesium halide or methyllithium to a solution of anhydrous di($C_1$-$C_3$alkoxy)titanium dichloride in an organic solvent and thereby generating the organometallic methylating agent.

In certain embodiments the method for synthesizing a 3α-hydroxy, 3β-methyl-5α-pregnan-20-one additionally comprises a methylating agent formed by adding about 1 to about 4 equivalents of methyl magnesium halide or methyllithim to a solution of $TiCl_4$ in an organ solvent.

In another preferred embodiment of the invention 0.75 to 4 molar equivalents of the iron organomettalic methylating agent (based on Dione 2 is reacted with dione 2 in an inert solvent.

In another preferred embodiment of the invention crude ganaxolone is purified by stirring the crude product in hot ethyl acetate to efficiently remove reaction impurities.

In the Experimental Section Table 1 summarizes various reaction conditions and stoichiometries with different organometallic reagents. Useful conversion of Dione 2 to ganaxolone can be effected with the use of different organometallic reagents under different reaction conditions. Table 2 summarizes optimization of parameters regarding purification of crude ganaxolone.

EXAMPLES

Analytical Methods
Mass Spectrometry
Mass spectra were obtained on an LC/MS system consisting of an HP 1100 LC separations module equipped with Thermo Finnigan LCQ-Deca mass detector. The ion source is ESI+/MS. The LC conditions are listed below.
Column: Waters Sunfire C18, 4.6(ID)×250(L) mm, 5 μm
Mobile phase: ACN/MeOH/$H_2O$=65/5/30 (Isocratic)
Run time: 40 min
Flow rate: 1 ml/min
Column Temperature: ambient
Detector: RI
Detector temperature: 40° C.
Injection volume: 50 ul.
HPLC
HPLC Analyses were carried out on a HITACHI L-2000 series or Waters 2695 separation module equipped with a Waters 2414 refractive index (RI) detector. The conditions are listed below:
Column: Waters Sunfire C18, 4.6(ID)×250(L) mm, 5 μm
Mobile phase: ACN/MeOH/$H_2O$=65/5/30 (Isocratic)
Detention time: 40 min
Flow rate: 1 ml/min
Temperature: ambient
Detector temperature: 40° C.
Injection volume: 50 ul
Sample concentrations to be injected are from 0.1 to 1 mg/ml in methanol.
NMR Spectroscopy
NMR spectra were obtained on a Bruker Avance 400 or an Oxford 300 NMR spectrometer in $CDCl_3$ or other deuterated solvents.
Purity
Crude and purified Ganaxolone purity is expressed by area percent for each reaction impurity and the relative Retention Time (RRT) to the desired product by HPLC analysis. % Yields are expressed as isolated yields.

Example 1

Anhydrous tetrahydrofuran (190 g) and 5α-pregnane-3,20-dione (1.0 g, 3.16 mmol) are charged to a dry 250 mL 3-necked round-bottomed flask under nitrogen to obtain a clear solution. The flask is then cooled to −30° C. (internal temperature) at which temperature methyllithium solution in diethoxyethane (3M, 1.1 mL, 3.3 mmol) is added via a syringe. The reaction is stirred at −25 to −20° C. under nitrogen for 1 h. Aliquot is quenched with 3N HCl and extracted with ethyl acetate. The organic layer is washed with 3N NaOH and water. Removal of solvent afforded a white solid, which is dissolved in methanol and analyzed by HPLC (Table 1, entry 1).

Example 2

Tert-butyl methyl ether (anhydrous, 30mL) chilled to −10° C. is added in a dropwise fashion to a well-stirred suspension of 5α-pregnane-3,20-dione (1.9 g, 6 mmol). The reaction mixture is held between 0° C. and 10° C. for 4 hours followed by 12 hours at 10-15° C. The reaction mixture is quenched by addition of 100 ml of 2N HCl and the products are extracted with 200 mL of ethyl acetate. The organic layer is washed with 2N NaOH and brine and the solvent are removed in vacuo to afford a complex mixture of products containing 30.1% of ganaxolone 1 by HPLC along with 0.99% starting 5α-pregnane-3,20-dione 2 (Table 1, entry 2).

Example 3

Titanium tetrachloride (350 uL, 3.2 mmol) is added in a dropwise fashion to a solution of titanium tetraethoxide (2.42 g, 10.6 mmol) in tetrahydrofuran (anhydrous, 30 mL) cooled to 0° C. After stirring for 20 min at 0° C., methyl magnesium chloride (3M, 4.3 mL 12.9 mmol) in tetrahydrofuran solution is added dropwise while maintaining the temperature below 5° C. After stirring for an additional 20 minutes at 5° C., 5α-pregnane-3,20-dione (2.53 g, 8 mmol) was added in one portion. The reaction is warmed to 40° C. and stirred for 4 hours. The reaction mixture is quenched with 20 mL of methanol and the solvent removed in vacuo. The reaction mixture is partitioned between 100 ml of 3N HCl and 100 mL of ethyl acetate. The organic layer is washed with 1N sodium hydroxide and brine and the solvent removed in vacuo to afford crude ganaxolone as a white solid of 75.9% pure ganaxolone by HPLC (Table 1, entry 3).

Example 4

A solution of ferric chloride (anhydrous, 2.14 g, 13.2 mmol) in tetrahydrofuran (anhydrous, 40 mL) is cooled to −50° C. Methyl magnesium chloride (3M, 17.6 ml, 52.8 mmol) in tetrahydrofuran is added to this mixture dropwise maintaining the internal temperature below −40° C. After 10 min at −40° C., 5α-pregnane-3,20-dione (3.48 g, 11 mmol) is added in one portion with stirring. The temperature is brought to −20° C. over 30 min. and stirred 2 hours. The reaction mixture is quenched with 100 ml of 2N HCl and the product extracted with 100 ml ethyl acetate. The organic layer is washed with 2N NaOH and brine and the solvent removed in vacuo to afford crude ganaxolone (80.2% purity by HPLC (Table 1, entry 4).

Example 5

A mixture of ferric chloride (anhydrous, 1.63 g, 10.06 mmol) in tetrahydrofuran (anhydrous, 35 ml) is cooled to −50° C. under nitrogen. Methyllithium (3M, 3.4 mL, 10.2 mmol) in diethoxymethane is added to the ferric chloride mixture, maintaining the temperature below −40° C. After this addition is complete methyl magnesium chloride solution (3M, 10.1 ml, 30.18 mmol) in tetrahydrofuran is added maintaining the internal temperature below −40° C. After 10 min. at −40° C., 5α-pregnane-3,20-dione (2.84 g, 9 mmol) is added in one portion with stirring. The temperature is brought to −20° C. and stirred for 3.5 hours. The reaction is quenched by addition of 3 ml of acetic acid and the tetrahydrofuran was removed in vacuo. The residue is partitioned between 100 ml of 3N HCl and 200 ml of ethyl acetate. The organic layer is washed with 1N sodium hydroxide and brine and the solvent is removed in vacuo to afford crude ganaxolone (94.8% purity by HPLC) (Table 1, entry 5)

Example 6

A reaction flask is charged with anhydrous lithium chloride solution in tetrahydrofuran (0.5M, 100 mL, 50 mmol). The reaction mixture is chilled to 0° C. and anhydrous ferric chloride (5.61 g, 34.6 mmol) was added in portions keeping the temperature below 10° C. The resulting pale green solution was cooled to −35° C. and methyl magnesium chloride solution in tetrahydrofuran (3M, 47 mL, 141 mmol) is added keeping the temperature below −30° C. After the addition is complete the reaction mixture is cooled to −35° C. and 5α-pregnane-3,20-dione (10 g, 31.65 mmol) is added with stirring keeping the temperature below −25° C. The reaction is allowed to warm to −20° C. and stirred at −18° C. to −22° C. for 3 hrs. At this time there was 0.96% starting material by HPLC and 94.46% ganaxolone (Table 1, entry 6). The reaction is quenched by the slow addition of 225 ml of 3N HCl keeping the temperature below 25° C. After the addition is complete the resulting suspension of ganaxolone is granulated overnight under nitrogen atmosphere. The reaction is filtered and the filter cake washed successively with 50 ml of 20% THF/3N HCl, 50 mL of 3N HCl, and twice with 50 ml of water. The filter cake is dried in a vacuum oven at 70° C. to afford 9.54 g (91% yield) of 99% pure ganaxolone 1 as a white solid.

Example 7

Tetrahydrofuran (anhydrous, 35 mL) is cooled to 10° C. and 907 mg (21.4 mmol) of lithium chloride (anhydrous) is added in one portion. The mixture is stirred for 10 min after which a clear solution is obtained. To this mixture is added Ferric Chloride (anhydrous, 1.62 g, 10 mmol) in one portion and stirred for an additional 5 min. The reaction mixture is then cooled to −35° C. and methyl magnesium chloride (3M, 13.3 ml, 40 mmol) in tetrahydrofuran is added dropwise maintaining the internal temperature between −35° C. and −30° C. After the addition is complete stirring is continued for 10 min. at −30° C. and 5α-pregnane-3,20-dione 2 (2.85 g, 9 mmol) is added in one portion with stirring. The internal temperature is allowed to rise to −20° C. and held between −15° C. and −20° C. for 2 hours. HPLC analysis of an aliquot demonstrated 1.2% starting material and 95.3% ganaxolone (Table 1, entry 7).

Example 8

Lithium chloride (1.43 g, 33.8 mmol) is added to tetrahydrofuran (anhydrous, 40 ml) at 10° C. and stirred until a solution is obtained. Ferric chloride (anhydrous, 1.63 g, 10.06 mmol) is added and stirred for 5 minutes. The reaction mixture is then cooled to −35° C. and methylmagnesium chloride solution (3M, 13.4 ml, 40.24 mmol) of in tetrahydrofuran is added while maintaining the internal temperature between −35° C. and −25° C. After the addition stirring is continued for 10 min at −30° C. and 5α-pregnane-3,20-dione (3.0 g, 9.5 mmol) is added in one portion with stirring. The internal temperature is allowed to rise to −20° C. and stirred between −15° C. and −20° C. for 2 hours. HPLC analysis of an aliquot demonstrated 1.47% starting material and 94.25% ganaxolone (Table 1, entry 8). The reaction is quenched by the slow addition of 2.4 mL (42 mmol) of acetic acid while maintaining the temperature below −10° C. After the addition is complete the reaction mixture is allowed to warm to room temperature with vigorous stirring. The tetrahydrofuran is then removed in vacuo and the resulting residue os partitioned between 3N HCl and ethyl acetate. The organic layer is washed with 2N NaOH and brine and the solvent removed in vacuo to afford 3.5 g of crude ganaxolone (98% purity by HPLC).

Example 9

THF (anhydrous, 190 g), LiCl (anhydrous, 4.2 g, 0.100 mol), and FeCl$_3$ (anhydrous, 10.8 g, 0.066 mol) under nitrogen are charged into a dry 500 mL 3-necked round-bottomed flask. MeMgCl (3M, 84.4 mL, 0.253 mol) in tetrahydrofuran is added while maintaining the internal temperature between 0° C. to 15° C. After completion of the addition, 5α-pregnane-3,20-dione (20 g, 0.0633 mol) is added in one portion and the resulting mixture is stirred between 0° C. to 15° C. under N$_2$. The reaction is monitored by HPLC as follows: an aliquot is quenched with 3N HCl and extracted with ethyl acetate. The organic layer is washed with 3N NaOH and water. Removal of solvent afforded a white solid, which is dissolved in methanol and analyzed by HPLC (Table 1, entry 9).

Example 10

THF (anhydrous, 80 g) and LiCl (anhydrous, 2.12 g, 50 mmol) are charged into a dry 500 mL 3-necked round-bottomed flask. The flask is cooled to −10° C. and FeCl$_3$ (anhydrous, 5.63 g, 34.8 mmol) is added. The mixture is cooled to −35° C. under nitrogen. MeMgCl solution in tetrahydrofuran (3M, 58 mL, 174 mmol) is added slowly while maintaining internal temperature between −27 to −35° C. during addition. After the addition, 5α-pregnane-3,20-dione (10 g, 31.6 mmol) is added in one portion and the resultant mixture is stirred between −25 to −20° C. under nitrogen. The reaction is monitored by HPLC as follows: an aliquot is taken, quenched with 3N HCl and extracted with ethyl acetate. The organic layer is washed with 3N NaOH and water and evaporated to dryness. The white residue is dissolved in methanol and analyzed by HPLC (Table 1, entry 10).

Example 11

THF (anhydrous, 120 g) and LiCl (anhydrous, 2.12 g, 50 mmol) are charged into a dry 500 ml 3-necked round-bottomed flak. The flask was cooled to −10° C. and FeCl$_3$ (anhydrous, 1.28 g, 7.9 mmol) was added. The mixture was cooled to −35° C. under nitrogen. MeMgCl solution in tetrahydrofuran (3M, 13.3 mL, 39.9 mmol) was added slowly while maintaining internal temperature between −27 to −35° C. during addition. After the addition, 5α-pregnane-3,20-dione (10 g, 31.6 mmol) was added in one portion and the resultant mixture was stirred between −25 to −20° C. under nitrogen. The reaction was monitored by HPLC as the following: an aliquot was taken, quenched with 3N HCl and extracted with ethyl acetate. The organic layer was washed with 3N NaOH, water and evaporated to dryness. The white residue was dissolved in methanol and analyzed by HPLC (Table 1, entries 11).

TABLE 1

Conversion of 5α-Preganane-3,20-Dione to Ganaxolone

| Entry | % (3) | % Dione (2) | % (5) | % C-20 mono (6) | % Ganaxolone (1) | % (4) | Reaction Conditions |
|---|---|---|---|---|---|---|---|
| RRT | 0.68 | 0.75 | 0.82 | 0.9 | 1 | 1.09 | |
| 1 | 8.64 | 39.94 | 13.13 | 9.98 | 11.16 | 18.06 | MeLi (1.0 eq.); −25° C. to −20° C., 1 h |
| 2 | 8.47 | 0.99 | 11.47 | 1.57 | 30.08 | 44.98 | Me$_3$Al (3.0 eq.); 0° C.-15° C., 16 h |
| 3 | 17.16 | 1.26 | 0.52 | ND | 75.86 | 2.06 | Ti(OEt)$_4$ (1.3 eq.), TiCl$_4$ (0.4 eq.), MeMgCl (1.6 eq.); 40° C. |
| 4 | 5.40 | 4.36 | 0.57 | 0.09 | 80.24 | 8.48 | FeCl$_3$ (1.2 eq.), MeMgCl (4.8 eq.); −40° C. to −20° C.; 2 h |
| 5 | 0.93 | 1.19 | ND | ND | 94.73 | 2.44 | FeCl$_3$ (1.1 eq.), MeLi (1.1 eq.), MeMgCl (3.3 eq.), PhOLi (1.0 eq.); −50° C. to −20° C. |
| 6 | 1.22 | 0.96 | ND | ND | 94.46 | 2.18 | FeCl$_3$ (1.1 eq.), LiCl (1.6 eq.), MeMgCl (4.4 eq.); −40° C. to −18° C. |
| 7 | 1.15 | 1.16 | ND | ND | 95.28 | 1.72 | FeCl$_3$ (1.1 eq.), LiCl (2.1 eq.), MeMgCl (4.0 eq.); −35° C. to −15° C. |
| 8 | 1.52 | 1.47 | ND | ND | 94.25 | 1.93 | FeCl$_3$ (1.0 eq.), LiCl (3.3 eq.), MeMgCl (4.0 eq,); −23° C. to −15° C. |
| 9[a] | 23.37 | 3.33 | 2.86 | ND | 58.06 | 5.12 | FeCl$_3$ (1.05 eq.), MeMgCl (4.0 eq.), LiCl (1.58 eq); 1 h, 0 to 15° C. |
| 10 | 1.33 | 1.29 | 0.47 | 0.31 | 70.92 | 24.5 | FeCl$_3$(1.1 eq.), MeMgCl (5.5 eq.), LiCl (1.58 eq); 1 h, −25 to −20° C. |
| 11[b] | 0.65 | 52.08 | 0.51 | ND | 45.44 | 0.18 | FeCl$_3$(0.25 eq.), MeMgCl (1.25 eq.), LiCl (1.58 eq); 1 h, −25 to −20° C. |

[a]Four additional unknown by-products were detected by HPLC.
[b]Reaction was not complete after 20 h with ca 30% of 3,20-dione starting material left.

Example 12A

THF (anhydrous, 9.65 kg) and LiCl (anhydrous, 0.21 kg) are charged into a $N_2$—purged 50-L Hastelloy reactor. The mixture is stirred under $N_2$ and cooled to −10° C. for 1 h. $FeCl_3$ (anhydrous, 0.515 kg) is charged into the reactor with stirring and the reaction mixture is cooled to −35° C. MeMgCl (3.0M, 4.04 kg) in tetrahydrofuran is slowly charged into the reactor while maintaining internal temperature at a target of −35° C. with stirring. After addition is complete, the reaction is stirred at −35° C. for one hour. 5α-Pregane-3,20-dione (1.00 kg) is charged into the reactor while maintaining the internal temperature about −35° C. After the addition, the reaction is warmed to −21° C. in about 1 h and stirred at the same temperature for 1 h. Glacial acetic acid (3.36 kg) is slowly charged into the reactor (1 h) and the reaction is warmed to about 25° C. (1 h). THF is removed by vacuum distillation with jacket temperature set at 35° C. to a final reaction volume of 7.8 L. The residue is cooled to about 0° C. followed by slow addition of 3N HCl (13.86 kg) while maintaining the internal temperature below 25° C. The reaction mixture is stirred at 25° C. for 6 h. The solid is collected by filtration and the product cake washed with 25% THF in water (w/w, 4.89 kg) once and water (5.0 kg) four times followed by a final wash with 25% THF/water (w/w, 4.86 kg). The wet cake is dried under vacuum at 50° C. to obtain crude ganaxolone (0.983 kg) with a purity of 95.5% by HPLC (Table 2, entry 1).

Example 12B

A 2-L 3-necked round-bottomed flask equipped with a mechanical stir, a 500 mL graduated additional funnel and low temperature thermometer is charged with anhydrous tetrahydrofuran (THF) (950 g) under nitrogen. The flask is cooled in a cold bath to about 0° C. (internal temperature) at which time lithium chloride (anhydrous, 21.2 g, 0.5001 mol) is added in one portion. The mixture is stirred while being cooled to −10° C. and ferric chloride (anhydrous, 51.3 g, 0.3165 mol) is added in one portion. The mixture is stirred to dissolve the solids while being cooled to −30° C. Methylmagnesium chloride (3 M, 394.2 g, 1.171 mol) in tetrahydrofuran is added slowly via the addition funnel maintaining internal temperature between −30° C. and −25° C. 5α-Pregane-3,20-dione (100 g, 0.3165 mol) is added in one portion and the reaction is stirred between −25 and −20° C. under nitrogen until completion (5 h) (<3% area by HPLC).

After reaction completion, acetic acid (320 ml) is added. The mixture is stirred until a solution is formed. THF is removed in vacuo to obtain a slurry (1016 g), which is stirred in 3N HCl (1250 mL) for 6 h. The resulting suspension is chilled in an ice-water bath for 2 h and filtered under vacuum. The wet cake is washed with cold 20% THF solution in water (v/v, 100 mL) and water (200 mL×3) to obtain the crude ganaxolone as a wet white solid (144 g) in 97.33% purity by HPLC (Table 2 entry 4).

Example 12C

THF (anhydrous, 106 mL), LiCl (anhydrous, 2.1 g, 0.050 mol) and $FeCl_3$ (anhydrous, 5.1 g, 0.0317 mol) are charged into a dry 250 mL 3-necked round-bottomed flask. The mixture is stirred under nitrogen while being cooled to about −25° C. Starting material 5α-Pregane-3,20-dione (10 g, 0.0316 mol) is added in one portion and the resultant suspension stirred for 5 min. Grignard MeMgCl (3M 39 mL, 0.117 mol) in tetrahydrofuran is added slowly while maintaining internal temperature between −25 to −20° C. After the addition, the dark brown reaction mixture is stirred under nitrogen at the same temperature overnight. HPLC analysis showed completion of reaction, with the dione being less than 1.37% and ganaxolone 92.71%.

The reaction is quenched by adding acetic acid (32 mL). The dark brown mixture is stirred while warming to obtain a light brown solution. The solution is concentrated by Rotovap to obtain a greenish residue (82 g), which is stirred with 3N HCl (125 mL) at ambient temperature for 1 h. The suspension is filtered under vacuum. The wet cake is washed with water (50 mL×2) and dried by suction. The wet crude ganaxolone is dissolved in THF (100 mL) at ambient temperature. The solution is clarified by filtering through a 0.45 μm membrane filter. The filtrate is concentrated by distillation at atmospheric pressure to remove most of the THF (ca 70%). While at reflux, water (150 mL) is added. The white suspension is stirred at reflux for 10 min. It is then cooled in an ice-water bath for 1 h. The solid is collected by filtration, washed with water and dried by suction.

The wet solid is slurried in ethyl acetate (50 mL) at 70° C. for 8 h and cooled in an ice-water bath for 1 h. The solid is filtered and washed with cold ethyl acetate (10 mL). After drying at 50° C. under vacuum, purified ganaxolone as obtained (8.3 g, 79% yield). Purity: 99.59% by HPLC.

Example 13A

Purification of Crude Ganaxolone

The crude ganaxolone of Example 12A (20 g) is slurried in ethyl acetate (120 mL) at 70° C. for 18 h. The crude slurry is removed from the heat and the suspension chilled in an ice-water bath for 1 h. The product is collected by filtration, washed with 20 mL of 2-propanol/water mixture (1;1, v/v) and dried to yield 16.6 g of ganaxolone. The purity of the purified ganaxolone was 99.71% with single largest reaction impurity being 0.07% (Table 2, entry 2).

Example 13B

Purified Ganaxolone

Purified ganaxolone, obtained by the method given in Example 13A (100 g) is dissolved in hot THF (700 ml). The solution is clarified while hot by filtration through a 0.45 μm filter (to remove insoluble materials). The solution is concentrated to remove about 370 mL of THF and the residue heated at reflux to obtain a clear solution. While at reflux, water (450 mL) is added slowly to induce precipitation. Heat is removed and the reaction stirred at 25° C. for 2 h. The reaction is further stirred at 0° C. for 2 h. The solid is collected by filtration and dried to obtain 96 g of ganaxolone with 97.2% purity. A portion of above clarified ganaxolone (20 g) is purified by stirring in ethyl acetate (100 mL) at 70° C. for 19 h. The ganaxolone is cooled and stirred at about 5° C. for 2 h and filtered. After drying, pure ganaxolone (17 g) is obtained with a purity of 99.83% and single largest reaction impurity present is 0.07% (Table 2, entry 3).

Example 13C

Wet crude ganaxolone (140 g) from Example 12B is stirred in a mixture of ethyl acetate (630 mL) and 2-propanol (70 mL) at 55° C. for 8 h and cooled to ambient temperature and further chilled in an ice-water bath for 2 h. The suspension is filtered under vacuum, washed with 50 mL of cold mixture of ethyl acetate/2-propanol/water (9:1:0.7, v/v/v) and dried in a vacuum oven at 60° C. to constant weight (76.2 g, 74.4% yield). The purity is 99.81% and no single impurity is greater than 0.1% by HPLC (Table 2, entry 5).

Example 13D

Crude ganaxolone (9 g) with a purity profile shown in Table 2 entry 6, prepared by a method similar to that described in Example 12A, is dissolved in a mixture of ethyl acetate (27 mL) and 2-propanol (63 mL) at reflux. Purified water (45 mL) is added and the resultant suspension is stirred at reflux for 10 min. Heating is removed and the suspension cooled in an ice-water bath for 1 h. The solid is collected by filtration. The wet cake is washed with 40 mL of 2-propanol/water mixture (1/2, v/v) and dried at 60° C. under vacuum for 63 h to obtain 7.78 g of purified ganaxolone. Its purity is 99.69% with single largest impurity being 0.08% (Table 2, entry 7).

Example 13E

Crude ganaxolone with a purity profile shown in Table 2, entry 8 is prepared by a method similar to that described in Example 12A except less $FeCl_3$ is added. The crude material (30 g) is dissolved in tetrahydrofuran (210 mL) at reflux. The solution is hot filtered through a filter paper to remove insoluble materials. The clear filtrate is concentrated in vacuo until approximately 100 g of tetrahydrofuran remains. The slurry is heated at reflux to dissolution. Water (135 g) is added slowly at reflux. The white suspension is stirred at reflux for 30 min and removed from heat. The suspension is cooled to room temperature and further chilled in an ice-water bath for 1 h. The solid is collected by filtration and dried at 50° C. under vacuum overnight to yield 28.5 g of product.

The above solid (28.5 g) is stirred in ethyl acetate (285 mL) at 70° C. for 4 h. The solid is stirred at room temperature for 2 h and chilled in an ice-water bath for 2 h. The solid is collected by filtration, washed with cold ethyl acetate (10 mL) and dried at 50° C. under vacuum overnight to obtain 21.5 g of product. This material is stirred two additional times in ethyl acetate (5 ml/g solid, 4 hour stirring) at 70° C. followed by cooling to 10° C. and filtered) to afford 17.5 g (58.3% yield) of purified ganaxolone. Its purity is 99.86% with single largest reaction impurity being 0.06% (Table 2 Entry 9).

TABLE 2

Purity Profiles of Ganaxolone Batches before and after Purifications

| Entry | Purity profile | Pregnanolone* | 20-dimethyl-20-hydroxy-5α-pregnane-3-ol** | 3-Epi (3) | 3,20-dione 2 | 3-Epi C-20 Methylation (5) |
|---|---|---|---|---|---|---|
| | RRT | 0.57 | 0.63 | 0.68 | 0.75 | 0.82 |
| 1 | Example 12A (crude) | 0.46 | 0.08 | 0.86 | 0.20 | ND |
| 2 | Example 13A (purified) | 0.05 | 0.07 | 0.05 | 0.03 | ND |
| 3 | Example 13B (purified) | 0.02 | 0.07 | 0.01 | ND | ND |
| 4 | Example 12B (crude) | 0.43 | 0.07 | 0.68 | 0.08 | ND |
| 5 | Example 13C (purified) | 0.03 | 0.04 | 0.05 | ND | ND |
| 6 | Example 13D (crude) | 0.27 | 0.08 | 0.45 | 0.45 | ND |
| 7 | Example 13D (puried) | 0.07 | 0.08 | 0.07 | 0.03 | ND |
| 8 | Example 13E (crude) | 0.45 | 0.03 | 0.59 | 0.57 | 0.05 |
| 9 | Example 13E (purified) | 0.03 | ND | 0.06 | ND | ND |

| Entry | C-20 methylation (6) | GNX1 | 4 | 7*** | UP | UP | UP | UP | UP |
|---|---|---|---|---|---|---|---|---|---|
| | 0.9 | 1.00 | 1.09 | 1.44 | 1.63 | 1.77 | 2.27 | 2.41 | 2.78 |
| 1 | ND | 95.57 | 1.35 | ND | 0.08 | 0.43 | 0.12 | 0.47 | 0.33 |
| 2 | ND | 99.71 | 0.07 | ND | ND | ND | ND | ND | ND |
| 3 | ND | 99.83 | 0.07 | ND | ND | ND | ND | ND | ND |
| 4 | ND | 97.33 | 0.59 | 0.06 | ND | 0.08 | ND | 0.67 | ND |
| 5 | ND | 99.81 | 0.06 | ND | ND | ND | ND | ND | ND |
| 6 | ND | 97.97 | 0.31 | ND | 0.09 | 0.38 | ND | ND | ND |
| 7 | ND | 99.69 | 0.06 | ND | ND | ND | ND | ND | ND |
| 8 | 0.03 | 88.79 | 9.23 | 0.06 | 0.07 | 0.12 | ND | ND | ND |
| 9 | ND | 99.86 | 0.06 | ND | ND | ND | ND | ND | ND |

*Carried over from 5α-Pregane-3,20-dione;
**Likely formed by methylation of the C20 carbonyl of pregnanolone;
***20-OH dehydration product of impurity 4;
UP: Unknown Product;
ND: Not Detected

Example 14

5α-Pregnane 3,20-dione (10 g) is reacted with a reagent obtained by reacting $FeCl_3$ (5.2 g) and MeMgCl (4 equiv, based on $FeCl_3$) in anhydrous tetrahydrofuran (200 mL) at −25° C. for 3 h. The reaction is quenched with acetic acid (32 ml). The reaction mixture is concentrated in vacuo and the residue is stirred with 3N HCl for 6 h. The solid is collected by filtration, washed with water and dried at 50° C. under vacuum to obtain crude ganaxolone. The crude product is dissolved in THF (33 mL) at reflux and filtered hot. The filtrate is added with water (45 mL) to obtain a suspension, which is collected by filtration, washed with water and dried. The dried product is further slurried in ethyl acetate (50 mL) at 70° C. for 19 h. The suspension is cooled to 0° C. and filtered, washed with cold ethyl acetate and dried to obtain ganaxolone.

Example 15

5α-Pregnane 3,20-dione (10 g) is reacted with a reagent obtained by reacting $FeCl_3$ (5.2 g) and MeMgCl (4 equiv, based on $FeCl_3$) in dioxane (anhydrous, 200 mL) at −25° C. for 5 h. The reaction is quenched with acetic acid (32 ml). The reaction mixture is concentrated in vacuo and the residue is stirred with 3N HCl for 6 h. The solid is collected by filtration, washed with water and dried at 50° C. under vacuum to obtain crude ganaxolone. The crude product is dissolved in THF (33 mL) at reflux and filtered hot. The filtrate is added with water (45 mL) to obtain a suspension, which is collected by filtration, washed with water and dried. The dried product is further slurried in ethyl acetate (50 mL) at 70° C. for 19 h. The suspension is cooled to 0° C. and filtered, washed with cold ethyl acetate. The ethyl acetate slurry step is repeated one more time to obtain purified ganaxolone.

Example 16

5α-Pregnane 3,20-dione (10 g) is reacted with a reagent obtained by reacting $FeCl_3$ (5.2 g) and MeMgCl (4 equiv, based on $FeCl_3$) in t-butyl methyl ether (anhydrous, 200 mf) at −25° C. for 3h. The reaction is quenched with acetic acid (32 ml). The reaction mixture is concentrated in vacuo and the residue is stirred with 3N HCl for 6 h. The solid is collected by filtration, washed with water and dried at 50° C. under vacuum to obtain crude ganaxolone. The crude product is dissolved in THF (33 mL) at reflux and filtered not. The filtrate is added with water (45 mL) to obtain a suspension, which is collected by filtration, washed with water and dried. The dried product is further slurried in ethyl acetate (50 mL) at 70° C. for 19 h, The suspension is cooled to 0° C. and filtered. The ethyl acetate slurry step was repeated second time to obtain purified ganaxolone.

Example 17

Ferrous chloride (4 g) is reacted with MeMgCl (3 equiv based on $FeCl_2$) in THF (anhydrous, 200 mL) at −25° C. under nitrogen. To this mixture is then added 5α-Pregnane 3,20-dione (10 g). The mixture is stirred at −25° C. for 4 h and is quenched by adding acetic acid (32 mL). The mixture is concentrated in vacuo and the residue is stirred in 3N HCl (200 mL) for 6 h. The solid is collected by filtration, washed with water and dried. The crude product is dissolved in THF (33 mL) at reflux and filtered hot. The filtrate is mixed with water (45 mL) and the solid is collected by filtration, washed with water and dried. The solid is further slurried in ethyl acetate (50 mL) at 70° C. for 19 h. It is cooled to 5° C. and filtered, washed with cold ethyl acetate and dried to obtain ganaxolone.

Example 18

Ferrous chloride (4 g) is reacted with MeLi (3 equiv. based on $FeCl_2$) in toluene (anhydrous, 200 mL) at −25° C. under nitrogen. 5α-pregnane 3,20-dione (10 g) is then added to this mixture. The mixture is stirred at −25° C. for 5 h. It is quenched by adding acetic acid (32 mL). The mixture is concentrated in vacuo and the residue is stirred in 3N HCl (200 mL) for 6 h. The solid is collected by filtration, washed with water and dried. The crude product is dissolved in THF (33 mL) at reflux and filtered hot. The filtrate is mixed with water (45 mL) and the solid is collected by filtration, washed with water and dried. The solid is further slurried in ethyl acetate (50 mL) at 70° C. for 8 h. It is cooled to 5° C. and filtered, washed with cold ethyl acetate and dried to obtain ganaxolone.

What is claimed is:

1. A method for the manufacture of 3α-hydroxy, 3β-methyl-5α-pregnan-20-one (ganaxolone) comprising
   reacting 5α-pregnane-3,20-dione (Dione 2);
   with an organometallic methylating agent in an inert solvent and thereby obtaining ganaxolone, wherein the organometallic methylating agent contains iron, titanium, or a combination thereof, and wherein the purity of the ganaxolone is greater than 80 percent area by HPLC.

2. A method for the manufacture of 3α-hydroxy, 3βmethyl-5α-pregnan-20-one (ganaxolone) comprising
   reacting 5α-pregnane-3,20-dione (Dione 2);
   with an organometallic methylating agent in an inert solvent to provide ganaxolone, wherein the organometallic methylating agent contains iron, titanium, or a combination thereof; and
   wherein the yield of ganaxolone is greater than 80 percent.

3. A method for obtaining 3α-hydroxy, 3β-methyl-5α-pregnan-20-one
   reacting 5α-pregnane-3,20-dione (Dione 2);
   with an organometallic methylating agent in an inert solvent; and thereby obtaining ganaxolone;
   wherein the organometallic methylating agent contains iron, titanium, or a combination thereof, and
   wherein the ganaxolone obtained contains less than 2 percent area by HPLC of any reaction impurity.

4. The method of claim 3, additionally comprising heating the obtained ganaxolone in an organic solvent to obtain purified ganaxolone, wherein the purified ganaxolone contains less than 0.1 percent area by HPLC of any reaction impurity.

5. The method of claim 4 wherein the ganaxolone obtained contains less than 0.1 percent area by HPLC of an impurity of the formula

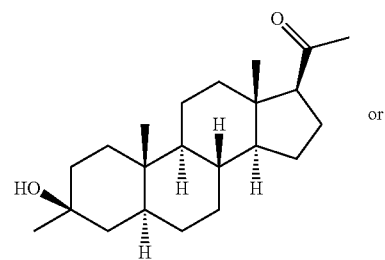

or

-continued

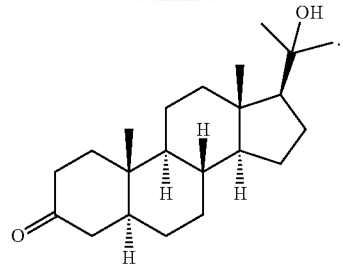

6. The method of claim 4, wherein the ganaxolone obtained contains less than 0.1 percent area by HPLC of an impurity of the formula:

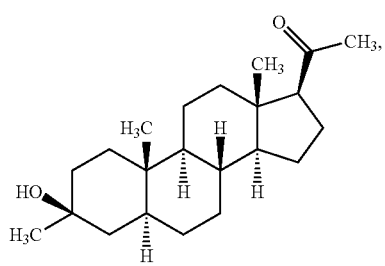

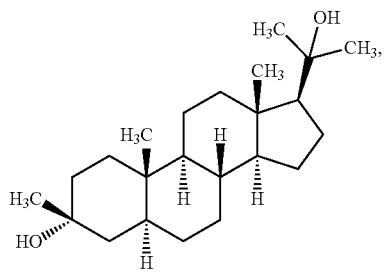

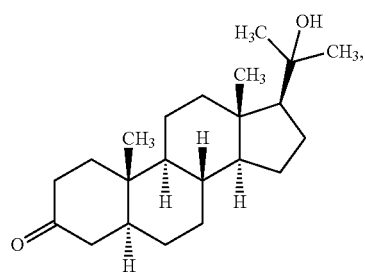

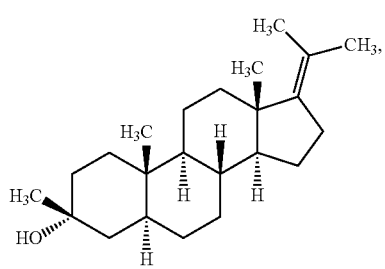

-continued

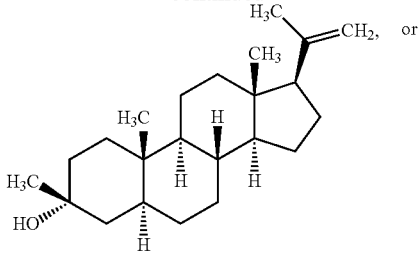

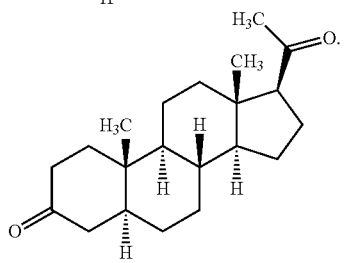

7. The method of claim 4 wherein the ganaxolone obtained contains less than 0.5% area by HPLC of an impurity of the formula:

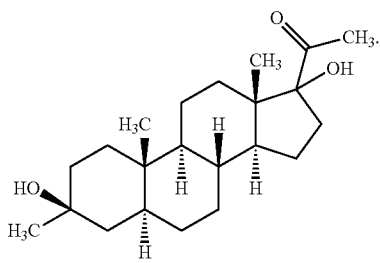

8. The method of claim 4 where the organic solvent is ethyl acetate and the amount of ethyl acetate utilized is 4-15 times the weight of the ganaxolone to be purified.

9. The method of claim 1, additionally comprising heating the obtained ganaxolone in an organic solvent wherein the purified ganaxolone obtained is greater the 99 percent pure by HPLC.

10. The method of claim 1, additionally comprising heating the obtained ganaxolone in an organic solvent wherein the % yield of purified ganaxolone obtained is greater than 55%.

11. The method of any one of claim 1, additionally comprising generating the organometallic methylating agent by adding about 2 to about 4 equivalents of methyl magnesium halide or methyl lithium to anhydrous ferric halide or anhydrous ferrous halide in an inert solvent, and thereby forming the organometallic methylating agent(s).

12. The method of claim 1, additionally comprising adding lithium chloride to the iron halide in the inert solvent prior to generating the organometallic methylating agent; wherein the amount of lithium chloride added is about 0.1 to about 4 equivalents of lithium chloride to equivalent of iron halide.

13. The method of claim 1 additionally comprising generating the organometallic methylating agent by adding about 1 equivalent of methylmagnesium halide or methyllithium to a solution of tri($C_1$-$C_3$alkoxy) titanium chloride in an organic solvent and thereby generating the organometallic methylating agent.

14. The method of claim 1 where the organometallic methylating agent is dimethyl iron ($Me_2Fe$), methyl triethoxy titanium, methylchloro diethoxy titanium (($CH_3$)Cl($CH_3CH_2O)_2Ti$), methyl trichlorotitanium ($CH_3Cl_3Ti$), tetramethyltitanium (($CH_3)_4Ti$), dimethyl dichloro titanium (($CH_3)_2Ti$), trimethyl chlorotitanium (($CH_3)_3ClTi$), or methyl iron chloride ($CH_3FeCl$).

15. The method of claim 1 wherein the organometallic methylating agent is an ate complex containing a $(Me)_3Fe^-$ anion and either lithium or MgX, as the cation, where X is a halide.

16. The method of claim 1 additionally comprising generating the organometallic methylating agent by adding about 1 equivalent of methylmagnesium halide or methyllithium to a solution of anhydrous di($C_1$-$C_3$alkoxy) titanium dichloride in an inertsolvent and thereby generating the organometallic methylating agent.

17. The method of claim 1 additionally comprising generating the organometallic methylating agent by adding about 1 to about 4 equivalent of methyl magnesium halide or methyllithium to $TiCl_4$ in an inert solvent and thereby generating the organometallic methylating agent.

18. The method of claim 1, wherein the inert solvent is tetrahydrofuran, glyme, t-butyl methyl ether, 1,4-dioxane, dimethoxyethane, or diethyl ether.

19. The method of claim 1 where methylmagnesium chloride is utilized to generate the organometallic methylating agent.

20. A method of claim 1 where methyllithium is utilized to generate the organometallic methylating agent.

21. The method of claim 1, wherein the inert solvent is maintained at a temperature of about −40° C. to about 35° C. during the reaction.

22. The method of claim 1, wherein the inert solvent is tetrahydrofuran and the inert solvent temperature is maintained a temperature of less than about −15° C. during the reaction.

23. The method of claim 1 wherein the organometallic methylating agent is

MeFeX, $Me_2Fe$, $Me_3Fe-Y+$ or $Me_4Fe(^{2-})2Y+$, methyl triethoxytitanium, MeCl($CH_3CH_2O)_2Ti$, $CH_3Cl_3Ti$, ($CH_3)_4Ti$, ($CH_3)Cl_2Ti$, or ($CH_3)_3ClTi$, or a combination of any of the foregoing; where Y+ is Li+ and/or [MgX]+; and X is Cl, Br or I.

* * * * *